(12) United States Patent
Rodriguez-Kabana

(10) Patent No.: US 6,720,352 B1
(45) Date of Patent: Apr. 13, 2004

(54) COMPOSITIONS AND PROCESS FOR NEMATODE CONTROL

(76) Inventor: Rodrigo Rodriguez-Kabana, 1026 E. Samford Ave., Auburn, AL (US) 36830

( * ) Notice: Subject to any disclaimer, the term of this patent is extended or adjusted under 35 U.S.C. 154(b) by 0 days.

(21) Appl. No.: 09/980,500

(22) PCT Filed: Apr. 3, 2000

(86) PCT No.: PCT/US00/08849

§ 371 (c)(1),
(2), (4) Date: Mar. 11, 2002

(87) PCT Pub. No.: WO00/67577

PCT Pub. Date: Nov. 16, 2000

(30) Foreign Application Priority Data

May 11, 1999 (SA) .............................. 98/10240

(51) Int. Cl.[7] ................ A61K 31/35; A61K 31/34; A61K 31/425; A01N 43/80
(52) U.S. Cl. ............... 514/451; 514/461; 514/372
(58) Field of Search ................. 514/322, 451, 514/461, 372

(56) References Cited

U.S. PATENT DOCUMENTS

| 4,943,307 A | * | 7/1990 | Detre et al. ................ 71/3 |
| 5,747,056 A | * | 5/1998 | Potter et al. ............ 424/410 |
| 6,051,233 A | | 4/2000 | Champon |

* cited by examiner

Primary Examiner—Alton N. Pryor
(74) Attorney, Agent, or Firm—Coleman R. Reap

(57) ABSTRACT

Chemical compositions having superior nematicidal properties are formulated. The compositions contain one or more selected aldehydes as the major component and one or more aliphatic or cyclic isothiocyanates as a minor component. Preferred mixtures contain furfural and one or both of methyl isothiocyanate and allyl isothiocyanate. Plant-parasitic nematodes are controlled by contacting the nematodes with the nematicidal compositions, by, for example, applying the compositions to soil or other plant growth media containing the nematodes.

30 Claims, No Drawings

COMPOSITIONS AND PROCESS FOR NEMATODE CONTROL

This application claims the benefit of PCT/US00/08849, which, in turn claims the benefit of South African provisional application No 98/10240, filed May 10, 1999.

TECHNICAL FIELD

This invention relates to novel compositions of aldehydes and isothiocyanates and their use for the enhancement of crop production, and more particularly to compositions of furfural or substituted furfurals and hydrocarbon isothiocyanates or substituted hydrocarbon isothiocyanates and their use for the control of phytoparasitic nematodes.

BACKGROUND ART

Most of the food produced in the world for human and animal consumption is grown from farm crops. As the population of the world increases it is becoming increasingly more difficult to produce adequate quantities of agricultural products to satisfy worldwide consumption demand. The situation is already critical because there is a limited amount of available arable land, and is becoming more and more critical each year as valuable farmland in the United States and other major crop-producing countries is converted to residential or industrial use.

Further aggravating the problem is the fact that plant pests, such as fungi, insects and nematodes destroy vast quantities of the plant crops. For example, it is estimated that in the tropic and subtropic regions of the world, plant-parasitic nematodes destroy up to fifty percent or more of the sprouts that are planted each year by feeding on the plants and/or infecting the plants with harmful diseases. Nematodes attack a wide variety of agricultural crops, such as soybeans, peanuts, strawberries, cotton, tobacco, squash, potatoes and other root vegetables, etc.

Because of the limited supply of fertile land, it is imperative that the productivity of existing farmland be increased. One way of accomplishing this is to reduce crop losses caused by plant pests by the use of biocides. Rodriguez-kabana, R., et al., in "Chemical and Biological Control", *Soilbome Diseases of Tropical Crops*, 1997, Chap. 17, pp. 397–418, present a history of plant pathogen control by treatment of pest-containing soil with chemical biocides. According to the authors, chemical treatment of crops for pest control has been practiced since the nineteenth century. Early biocides include carbon disulfide, formaldehyde and trichloronitromethane (chloropicrin). Later developed, more highly effective pesticides include halogenated hydrocarbons, such as methyl bromide, ethylene dibromide (EDB), and 1,2-dibromo-3-chloropropane (DBCP). EDB and DBCP have been banned for use as pesticides in several industrialized countries because of their carcinogenicity or mutagenicity, and methyl bromide has been scheduled for removal from the market in the United States because of its harmful effect on the ozone layer.

Moje, W, "The Chemistry and Nematocidal Activity of Organic Halides", *Advances in Pest Control Research*, Vol III, 1960, pp. 181–212, describes isothiocyanates as effective against nematodes and other soil-inhabiting organisms (pp. 207–209).

More recently, aldehydes, such as furfural, benzaldehyde and citral have been described as useful for plant pathogen control. For example, U.S. Pat. No. 5,084,477 discloses the use of furfural as a nematicide.

Compositions of aldehydes and various chemical compounds have been used for a variety of applications. German Patent No. 448, 446 discloses the use of water-soluble furfural and a respiratory or contact poison, such as pyrethrum or nicotine extract as an agent for combating insect plant pests; U.S. Pat. No. 4,440,783 discloses the use of a combination of allyl isothiocyanate or lower alkyl isothiocyanates with lemon grass oil and/or an odor masking agent, which may be benzaldehyde, to repel animals from garbage; and U. S. Pat. No. 5,703,124 discloses and antimicrobial composition comprising allyl isothiocyanate and a polyhydric alcohol which may contain aldehyde groups, the polyhydric alcohol enhancing the water solubility of the allyl isothiocyanate. Japanese Patent No. 11269010, issued Oct. 5, 1999 and reported in Chemical Abstract No. 1999:629918, discloses compositions comprised of a substituted glyoxylohydroximoyl chloride, an antifungal agent, which may be glutaraldehyde, and an antibacterial agent, which may be an alkylene bis(isothiocyanate). These compositions were found to control bacteria and fungi in white water in paper manufacturing. Farghally et al., in J. Pharm. Belg. (1985), 40(6), 366–72 report the synthesis of selected quinolinecarboxyaldehyde hydrazone derivatives by the reaction of quinolinecarboxyaldehyde hydrazones with, for example, phenylisothiocyanate (Chemical Abstract No. 1987:84461). The synthesized compounds were found to have no antibacterial activity. U.S. Pat. No. 6,051,233 discloses the use of compositions containing mustard oil, including allyl isothiocyanate, for soil treatment. These compositions additionally contain a heat component which may be, for example cinnamic aldehyde or benzaldehyde.

There is a continuing need to find more effective plant pathogen control agents. This invention provides new compositions that are highly effective as nematicidal agents.

DISCLOSURE OF INVENTION

According to a first broad embodiment, the invention comprises a composition comprised of (a) at least one heterocyclic aldehyde containing 4 to 25 carbon atoms, and (b) at least one isothiocyanate containing 2 to 18 carbon atoms or precursor thereof.

In a preferred aspect of the first embodiment, the least one heterocyclic aldehyde contains 4 to 12 carbon atoms and said at least one isothiocyanate or precursor thereof comprises an aliphatic isothiocyanate containing 2 to 14 carbon atoms, a precursor of an aliphatic isothiocyanate containing 2 to 14 carbon atoms, a cyclic isothiocyanate containing 5 to 12 carbon atoms, a precursor of a cyclic isothiocyanate containing 5 to 12 carbon atoms or mixtures thereof.

In another preferred aspect of the first embodiment, the at least one heterocyclic aldehyde contains oxygen, nitrogen, sulfur, phosphorus or combinations thereof, the at least one isothiocyanate or precursor thereof additionally contains oxygen, phosphorus, additional nitrogen, additional sulfur, or combinations thereof, or the heterocyclic aldehyde contains oxygen, nitrogen, sulfur, phosphorus or combinations thereof and the isothiocyanate or precursor thereof contains oxygen, phosphorus, additional nitrogen, additional sulfur, or combinations thereof.

In another preferred aspect of the first embodiment, the heterocyclic aldehyde is a formyl cyclic ether.

In another preferred aspect of the first embodiment, the at least one heterocyclic aldehyde comprises furfural, 2,5,-diformyl furan, formyl pyran, formyl tetrahydrofuran, formyl pyridine, or mixtures thereof, and the at least one isothiocyanate or precursor thereof comprises methyl isothiocyanate, ethyl isothiocyanate, propyl isothiocyanate, butyl isothiocyanate, allyl isothiocyanate, phenyl isothiocyanate, benzyl isothiocyanate sodium N-methyidithiocarbamate, tetrahydro-3,5-dimethyl-2H-1,3,5-thiadiazin-2-thione or mixtures thereof.

In another more preferred aspect of the first embodiment, the at least one heterocyclic aldehyde thereof comprises furfural, 2,5,-diformyl furan, or mixtures thereof, and the at least one isothiocyanate or precursor thereof comprises methyl isothiocyanate, allyl isothiocyanate, sodium N-methyldithiocarbamate, tetrahydro-3,5-dimethyl-2H-1,3,5-thiadiazin-2-thione or mixtures thereof.

In another preferred aspect of this embodiment, the at least one isothiocyanate is present as a component of mustard oil.

In another preferred aspect of the first embodiment, the composition further comprises a carrier system for the heterocyclic aldehyde, the isothiocyanate or both the heterocyclic aldehyde and the isothiocyanate.

In another preferred aspect of the first embodiment, the composition is in the form of a solution, a suspension or an emulsion. Preferably, it is in the form of an aqueous solution, suspension or emulsion.

In another preferred aspect of the first embodiment, the composition further comprises an oil.

In another preferred aspect of the first embodiment, the composition comprises about 50 to about 99.5 parts of heterocyclic aldehyde and about 0.5 to about 50 parts of total isothiocyanate or precursor thereof per each 100 parts of total heterocyclic aldehyde or precursor thereof and isothiocyanate or precursor thereof present in the composition.

In another preferred aspect of the first embodiment, the composition comprises about 80 to about 97 parts of heterocyclic aldehyde and about 3 to about 20 parts of isothiocyanate or precursor thereof per each 100 parts of total aldehyde or precursor thereof and isothiocyanate or precursor thereof present in the composition.

In another preferred aspect of the first embodiment, the composition comprises (a) furfural and (b) methyl isothiocyanate, allyl isothiocyanate, sodium N-methyidithiocarbamate, tetrahydro-3,5-dimethyl-2H-1,3,5-thiadiazin-2-thione or mixtures thereof and the composition comprises about 85 to about 95 parts of (a) and about 5 to about 15 parts of (b) per each 100 parts of (a) and (b) present in the composition.

According to a second broad embodiment, the invention comprises a method of controlling plant pests comprising introducing a composition comprised of at least one aldehyde containing 1 to 25 carbon atoms and at least one isothiocyanate containing 2 to 18 carbon atoms or precursor thereof into the environment containing the plant pests.

In a preferred aspect of the second embodiment, the method is carried out by applying the composition to plant growth medium containing said plant pests. Preferably, the plant growth medium comprises soil.

In a preferred aspect of the second embodiment, the at least one aldehyde comprises an aliphatic aldehyde containing 3 to 12 carbon atoms, a cyclic aldehyde containing 5 to 14 carbon atoms, or mixtures thereof, and the at least one isothiocyanate or precursor thereof comprises an aliphatic isothiocyanate containing 2 to 14 carbon atoms, a precursor of an aliphatic isothiocyanate containing 2 to 14 carbon atoms, a cyclic isothiocyanate containing 5 to 12 carbon atoms, a precursor of a cyclic isothiocyanate containing 5 to 12 carbon atoms or mixtures thereof.

In another preferred aspect of the second embodiment, the at least one aldehyde or precursor thereof comprises furfural, 2,5-diformyl-furan, formyl pyran, benzaldehyde, or mixtures thereof, and the at least one isothiocyanate or precursor thereof comprises methyl isothiocyanate, sodium N-methyldithiocarbamate, tetrahydro-3,5-dimethyl-2H-1,3,5-thiadiazin-2-thione, allyl isothiocyanate, or mixtures thereof.

In another preferred aspect of the second embodiment, the composition is applied to the plant growth medium prior to planting plants or seed therein.

In another preferred aspect of the second embodiment, the plant pests treated comprise nematodes.

In another preferred aspect of the second embodiment, sufficient composition is applied to the plant growth medium to provide a concentration of about 0.1 to about 1000 parts by weight of total aldehyde or precursor thereof and isothiocyanate or precursor thereof per each million parts by weight of medium being treated.

In another preferred aspect of the second embodiment, sufficient composition is applied to the medium to provide a concentration of about 0.5 to about 500 parts by weight of total aldehyde or precursor thereof and isothiocyanate or precursor thereof per each million parts by weight of medium being treated.

In a more preferred aspect of the second embodiment, the plant growth medium comprises soil and the composition comprises (a) furfural and (b) methyl isothiocyanate allyl isothiocyanate, sodium N-methyldithiocarbamate, tetrahydro-3,5-dimethyl-2H-1,3,5thiadiazin-2-thione or mixtures thereof, and sufficient composition is applied to the soil to provide a concentration of about 1 to about 100 total parts by weight of (a) and (b) per each million parts by weight of soil being treated. In another more preferred aspect, the composition comprises (a) furfural and (b) methyl isothiocyanate, allyl isothiocyanate or mixtures thereof, and sufficient composition is applied to the soil to provide a dosage of about 2 to about 500 kg of (a) plus (b) per each hectare of soil being treated.

In another preferred aspect of the second embodiment, the method comprises separately applying the aldehyde or precursor thereof and the isothiocyanate or precursor thereof to the plant growth medium.

BEST MODE FOR CARRYING OUT THE INVENTION

The invention comprises, as novel aspects, compositions of one or more selected aldehydic compounds and one or more selected isothiocyanate compounds, and the use of these compositions for the control of plant pests. The compositions are particularly effective for the control of plant-parasitic nematodes present in the soil in which plants or plant seeds are planted. It has been discovered that the compositions of the invention exhibit synergism when used as plant pest control agents in that they control plant pests more effectively than any of the active components of the compositions used individually at the same dosage rates. Thus, there is a significant economic incentive to use the compositions of the invention for pest control, particularly for plant parasitic nematode control.

Considering the compositions useful in the method of the invention in more detail, the aldehyde component may be any one or more organic compounds having one or more aldehyde groups, including aliphatic or alicyclic compounds, i.e., cycloaliphatic compounds, typically containing up to 25 carbon atoms. The aldehyde may contain more than 25 carbon atoms, particularly in the case of polymeric compounds or compounds having multiple aldehyde groups, but it is generally preferred to use aldehydes having not more than 25 carbon atoms, since these compounds are generally more readily available and less expensive than higher molecular weight aldehydes. Additionally, the aldehyde component may contain hetero atoms in addition to the aldehydic oxygen atom(s) of these compounds. Suitable hetero atoms include oxygen, nitrogen, sulfur, phosphorus and combinations of two or more of these. The most preferred hetero atom is oxygen.

Aliphatic aldehydic compounds useful in the compositions and/or method of the invention include straight- or branched-chain compounds, and they can be fully saturated or they can contain ethylenic unsaturation. Preferred aliphatic aldehydes contain up to 12 carbon atoms, and generally contain from 3 to 12 carbon atoms. In more preferred embodiments of the invention, the aldehyde component, when aliphatic, contains 4 to 8 carbon atoms. Typical saturated aliphatic compounds include propanal, butanal, pentanal (valeraldehyde), glutaraldehyde, hexanal, heptanal, octanal, 2-methyl-hexanal, 2,3-dimethyl-decanal, 2-hydroxy-hexanal, 3-amino-heptanal, etc. Suitable ethylenically unsaturated aliphatic compounds include propenal, butenal (crotonaldehyde), hexenal, 2-sulfo-octenal, citral, etc. Preferred aliphatic aldehydes include butyraldehyde, craotonaldehyde, valeraldehyde, glutaraldehyde, hexanal, heptanal, octanal and mixtures of any of these.

Cyclic aldehydic compounds included as compositions and/or in the method of the invention may be homocyclic, i.e., compounds whose ring atoms are carbon atoms only, or heterocyclic, i.e., compounds whose ring atoms contain atoms other than carbon atoms. Typical cyclic aldehydes are those containing 3 to 25 carbon atoms, and preferred cyclic aldehydes have 4 to 12 carbon atoms. Particularly preferred cyclic aldehydes are heterocyclic aldehydes containing 4 to 8 carbon atoms, especially the cyclic ethers. Suitable alicyclic compounds include cyclohexanal, cyclohexenal, 3-methyl-cyclohexanal, 4-hydroxy-cycloheptanal, 1,3-cyclohexanedial, saturated and unsaturated formyl cyclic ethers, such as furfural, 2,5-diformyl-furan, the formyl tetrahydrofurans, the formyl pyrans, etc. Suitable aromatic compounds useful in the method of the invention include benzaldehyde, 1,4-diformyl benzene, 2-formyl-naphthene, cinnamaldehyde, salicylaldehyde, etc. Suitable aromatic heterocyclic compounds include the formyl pyridines, etc. Preferred alicyclic aldehydes are those containing 5 ring atoms, one or more of which can be a hetero atom, such as oxygen, nitrogen, sulfur, phosphorus or combinations of these. More preferred aldehydes are the saturated and unsaturated formyl cyclic ethers, particularly furfural, 2,5-diformyl furan, precursors of these, and mixtures of any two or more of these. The most preferred aldehyde is furfural.

The isothiocyanate may be any one or more organic compounds having one or more isothiocyanate groups, including aliphatic or cyclic compounds typically containing 2 to 14 carbon atoms. This component may contain more than 14 carbon atoms, but it is generally preferred to use isothiocyanates having not more than 14 carbon atoms, since, like the aldehyde compounds, the lower molecular weight isothiocyanates are generally more readily available and less expensive than higher molecular weight isothiocyanates. Again, like the aldehyde component, the isothiocyanate component may contain hetero atoms in addition to the isothiocyanate sulfur atom(s) of these compounds. Suitable hetero atoms include oxygen, nitrogen, sulfur, phosphorus and combinations of two or more of these.

Aliphatic isothiocyanate compounds useful in the compositions of the invention include straight-chain or branched-chain compounds, and they can be fully saturated or they can contain ethylenic unsaturation. Preferred aliphatic isothiocyanates contain 2 to 14 carbon atoms, and the more preferred aliphatic isothiocyanates are those containing 2 to 12 carbon atoms. Typical saturated aliphatic compounds and precursors thereof include methyl isothiocyanate, propyl isothiocyanate, pentyl isothiocyanate, octyl isothiocyanate, 2-methyl-hexyl isothiocyanate, 2,3-dimethyl-decyl isothiocyanate, 2-hydroxy-hexyl isothiocyanate, 3-amino-heptyl isothiocyanate, sodium N-methyldithiocarbamate, tetrahydro-3,5-dimethyl-2H-1,3,5thiadiazin-2-thione, alkylene bis(isothiocyanates), such as methylene bis(isothiocyanate), ethylene bis(issthiocyanate), etc. Suitable ethylenically unsaturated aliphatic compounds include allyl isothiocyanate, butenyl isothiocyanate, 2-sulfohexenyl isothiocyanate, etc. Preferred aliphatic isothiocyanates and precursors thereof include methyl isothiocyanate, allyl isothiocyanate, sodium N-methyidithiocarbamate, tetrahydro-3,5-dimethyl-2H-1,3,5-thiadiazin-2-thione and mixtures of these. The isothiocyanate component(s) of the composition of the invention may be pure components, or they may be present as components of commercially available compositions, such as mustard oil.

Like the cyclic aldehydes, the cyclic isothiocyanate compounds useful in the compositions of the invention may be any of several types. They may be alicyclic; aromatic, for example, aryl, or substituted aryl, e.g., alkaryl, aralkyl; heterocyclic, etc. Typical useful cyclic isothiocyanates include those containing 5 to 12 carbon atoms, and preferred cyclic isothiocyanates have 5 to 10 carbon atoms. Typical alicyclic compounds include cyclohexyl isothiocyanate, cyclohexenyl isothiocyanate, 3-methyl-cyclohexyl isothiocyanate, 4hydroxy-cyclohexyl isothiocyanate, 1,3-clohexane diisothiocyanate, etc. Aromatic isothiocyanates useful in the invention include phenyl isothiocyanate, benzyl isothiocyanate, 4-methyl-benzyl isothiocyanate, 1,4-diisothiocyanato benzene, furyl isothiocyanate, etc. Preferred cyclic isothiocyanates include furyl isothiocyanate, phenyl isothiocyanate, benzyl isothiocyanate and mixtures of any of these.

As noted above, the combination of pesticides used in the invention makes it possible to achieve the same nematicidal effect with a lower overall dosage of pesticide than would be the case if either component of the combination were used alone. The invention is effective over a wide range of ratios of total aldehyde component to total isothiocyanate component. In general, compositions comprise about 50 to about 99.5 parts of total aldehyde component and about 0.5 to about 50 parts of total isothiocyanate component per each 100 parts of total aldehyde component plus total isothiocyanate component present in the compositions, i.e., per each 100 parts of the total of all aldehyde components and all isothiocyanate components present in the compositions of the invention or used in the method of the invention. Unless otherwise indicated, parts, percentages and ratios are to be construed as being on a weight basis. The compositions of the invention can be used at aldehyde and isothiocyanate concentrations outside of the above-stated ranges, however, in such case results may be less satisfactory than when the component concentrations are in the stated ranges. In preferred embodiments of the invention, the compositions comprise about 80 to about 97 total parts of aldehyde component and about 3 to about 20 total parts of isothiocyanate component per each 100 total parts of aldehyde components plus isothiocyanate components, and more preferably, the compositions comprise about 85 to about 95 total parts of aldehyde component and about 5 to about 15 total parts of isothiocyanate component per each 100 total parts of aldehyde components plus isothiocyanate components.

The invention can be used to control a variety of plant pests. As used herein the term "plant pests" is defined as any of the various small invertibrate animals which are harmful to plants, plant seeds, etc., including nematodes, insects, slugs, micro arthropods, protozoa, and their eggs and larvae, etc. Since the compositions of the invention are principally intended for use as nematicides, the method of the invention will be described in particular detail as it applies to the control of plant-harmful nematodes. The nematodes that are controlled by the invention may be of various types; for example, they may be waterborne or soilborne. The invention can be used to hinder the attack of nematodes on plants grown in an aqueous environment, i.e., hydroponically, or plants grown in a solid substrate, such as soil, or an artificial plant substrate medium, such as sand, peat moss, straw, etc. The substance in which the plants are grown and protected will be generally referred to herein as plant growth medium or simply as medium, and this term is intended to include any substance in which plants are grown.

The aldehyde-isothiocyanate compositions of the invention can be used in the invention in a number of ways. The aldehyde and isothiocyanate components of the compositions may be combined and applied as a mixture in the treatment methods of the invention, or they may be applied separately, with the isothiocyanate component(s) being applied before, during or after application of the aldehyde component(s). Furthermore, they may be applied in neat form or they may be combined with a carrier system. It is generally preferred to use them with a carrier system since it would likely be too costly and inefficient to apply the compositions without dilution. The compositions have been found to be highly effective at very low concentrations.

The carrier system may be in any suitable form, for example it may serve as a solvent for either or both of the aldehyde component(s) and the isothiocyanate component (s), i.e., active components, or it may be combined with the active ingredients as a suspension or emulsion. When the composition is formulated as a solution, the solvent may be an aqueous liquid, for example water or an aqueous alcoholic solution, or it may be an organic solvent, such as a petroleum distillate or higher hydrocarbon, e.g., an oil. It is preferred that the carrier system be comprised of substances that will readily dissipate into the environment to avoid accumulation of these substances in the medium being treated. When the ingredients are miscible liquids, it may be preferable to combine them as a mixture of the desired proportions and transport them in this form to the point of application. In cases in which the active components are not readily miscible or are solid, but are both soluble in a particular solvent, such as water, it may be preferable to prepare a concentrated solution of the components in the solvent and transport the concentrate to the point of application for dilution to the desired application concentration on site. In cases where one or both of the components are not readily soluble in suitable liquids, it may be preferable to prepare a suitable emulsion of the insoluble components in a carrier system, using suitable emulsifying agents where necessary or desirable. In some cases, it may be preferred to form an aerosol of the components for application by fumigation methods. This is particularly advantageous in cases in which the components are volatile or can be easily suspended as droplets in a carrier gas. In any event, the particular form of the composition is not critical to the invention.

The compositions of the invention can be applied to the nematodes or medium being treated in any desired manner. They can be sprayed over the surface of the medium being treated. This method is particularly effective when the compositions are readily soluble in a liquid, such as water, and where the roots of the plants being treated will not be very deep in the planting medium. Treatment compositions can also be applied to, for example, soils by trickling solutions or emulsions of the compositions through an irrigation system on the surface of or submerged in the soil. This method may be preferable where the roots of the plants to be protected are deeply planted, for example, to a depth of about ten centimeters. A third treatment method is fumigation. This method may preferable when the compositions can be readily gasified or formed into an aerosol and where it is only necessary to control pests which are located several centimeters below the surface of the soil. The method of application of the compositions of the invention to the plant pests or to medium containing the pests forms no part of the present invention.

The appropriate time to apply the compositions to the plant pests or to substrates harboring the pests will depend upon certain factors, including the particular compositions being applied. If the compositions are not phytotoxic, i.e., not harmful to the plants being protected, they may be applied at the time of planting or before or after planting. On the other hand, if they may be harmful to the plants, they are preferably applied several days or weeks prior to planting, so that they will have the desired effect on the target plant pests, but will dissipate before planting of the treatment composition-susceptible plants.

It will be appreciated that it is within the scope of the present invention to monitor and automatically regulate the application of the compositions of the invention to the medium being treated so that the invention can be practiced in an efficient manner.

The invention is further illustrated by the following examples. In those examples in which a diluent was used to prepare the base nematicide solution, acetone was selected as the diluent since it has negligible nematicidal activity at the concentrations used in the examples. The salad bowl nematode extraction technique used in each example is a standard nematological analysis procedure (Rodriguez-Kabana & Pope, 1981, Nematropica 11:175–185) comprising the following steps: A 100 mg sample of nematode-containing soil is spread evenly over the surface of tissue paper positioned on a one mm mesh circular sieve. The sieve is placed in an ordinary salad bowl and sufficient water to just cover the soil sample is introduced into the salad bowl. The soil sample is soaked in the water for 72 hours, during which period substantially all live nematodes migrate from the soil phase into the aqueous phase. At the end of the 72 hour period the sieve is removed from the salad bowl and the water in the bowl is filtered through a 38 micron sieve. All nematodes in the water are retained on the sieve. The nematodes are then rinsed from the sieve and into a counting dish and the nematodes are counted. The data obtained in the experiments were analyzed according to standard procedures for variance analysis. When F values were significant, Fisher's least significant differences were calculated according to standard procedures. Unless otherwise stated, all differences referred to were significant at the 95% or higher level of probability.

EXAMPLE 1

This example compares the nematicidal activity of nematicidal compositions containing furfural-mustard oil mixture (Composition A), furfural (Composition B) and mustard oil (Composition C) as the active ingredient(s). Composition A is an aqueous emulsion comprising 80 mls of demineralized water and 20 mls of emulsion concentrate comprising 20 volume % of an emulsifier and 80 volume % of a base nematicide solution comprised of 80 volume % furfural and 20 volume % mustard oil. Composition B is an aqueous emulsion comprising 80 mls of demineralized water and 20 mls of emulsion concentrate comprising 20 volume % of an emulsifier and 80 volume % of a base nematicide solution comprised of 80 volume % furfural and 20 volume % acetone. Composition C is an aqueous emulsion comprising 80 mls of demineralized water and 20 mls of emulsion concentrate comprising 20 volume % of an emulsifier and 80 volume % of a base nematicide solution comprised of 80 volume % acetone and 20 volume % mustard oil.

Soil samples were prepared from cotton field sandy clay loam having a pH of 6.2 and containing less than 1% organic matter and which was heavily infested with the plant pathogenic nematode rotylenchulus reniformis (reniform nematode). The soil, which had a moisture content of 60% field capacity, was sieved through a 1 mm mesh sieve and thoroughly mixed with washed fine ($\leq$1 mm mesh) siliceous river sand. Each soil sample comprised one kg of the above-described soil-sand mixture, placed in a 3 liter plastic bag.

A series of experiments was conducted by applying test compositions A, B or C to the bagged soil samples at dosages of 0.25, 0.50, 0.75 and 1.00 ml of the emulsions per bag, which dosages correspond, respectively, to active ingredient concentrations per kg of soil-sand mixture of 0.040, 0.080, 0.120, and 0.160 ml for Composition A experiments; 0.032, 0.064, 0.096 and 0.128 ml for Composition B experiments; and 0.008, 0.016, 0.024, and 0.032 ml for Composition C experiments. Thus, at each concentration level the concentration of a given component in Composition A was equal to the concentration of that component in Composition B or Composition C. The series also included a control sample which contained no nematicide. Sufficient samples were prepared to provide 8 replications of each treatment concentration. The nematicide-containing soil samples were thoroughly mixed to uniformly distribute the nematcide throughout the soil, and the mixed samples were put into one liter greenhouse plant pots and kept moist for one week. At the end of the one week period, a one hundred cc sample of the soil in each pot was subjected to nematological analysis by the salad bowls extraction technique. The average number of live nematodes in the replicated experiments for each treatment concentration was determined and recorded in Table I.

TABLE I

| Amount of emulsion added (ml/kg soil) | Reniform Nematodes per 100 cc of Soil | | | | |
|---|---|---|---|---|---|
| Composition | 0.00 | 0.25 | 0.50 | 0.75 | 1.00 |
| A | 737 | 310 | 43 | 1 | 1 |
| B | 737 | 623 | 596 | 498 | 526 |
| C | 737 | 601 | 77 | 5 | 0 |

This example shows that for reniform nematode control the combination of furfural and mustard oil provides decidedly more effectiveness than either furfural or mustard oil alone, when applied at the lowest dosage rate (0.25 ml/kg of soil). At this rate the use of Composition A resulted in about a 58% reduction in the number of reniform nematodes, the use of Composition B resulted in about a 15.5% reduction in the number of reniform nematodes and the use of Composition C resulted in about an 18.5% reduction in the number of reniform nematodes.

EXAMPLE 2

This example compares the nematicidal activity of nematicidal compositions containing furfural-benzaldehyde-methyl isothiocyanate mixture (Composition D), furfural-benzaldehyde mixture (Composition E) and methyl isothiocyanate (Composition F) as the active ingredient(s).

The procedure of Example I was repeated with the following changes: Composition D comprised 99 volume % of a 50-50 volume % mixture of furfural and benzaldehyde and 1 volume % of methyl isothiocyanate; Composition E comprised 99 volume % of a 50-50 volume % mixture of furfural and benzaldehyde and 1 volume % of acetone; Composition F comprised 1 volume % of methyl isothiocyanate and 99 volume % of acetone. The nematicide-containing soil samples were kept in the moistened state for 11 days before analysis. Compositions D, E and F were applied neat (not as an emulsion) directly to the soil without emulsifier at dosages of 0.0, 0.1, 0.2, 0.4 and 0.8 ml per kg of soil. These application rates correspond, respectively, to 0.0, 0.1, 0.2, 0.4 and 0.8 ml of furfural-benzaldehyde-methyl isothiocyanate mixture (Composition D) per kg of soil; 0.0, 0.099, 0.198, 0.396 and 0.792 ml of furfural-benzaldehyde (Composition E) per kg of soil; and 0.0, 0.001, 0.002. 0.004, and 0.008 ml of methyl isothiocyanate (Composition F) per kg of soil. Thus, at each concentration level the concentration of a given component in Composition D was equal to the concentration of that component in Composition E or Composition F. There were 5 replications of each experiment. At the end of the 11 day period, a one hundred cc sample of the soil in each pot was subjected to nematological analysis by the salad bowl extraction technique. The average number of live nematodes in the replicated experiments for each treatment concentration was determined and recorded in Table II.

TABLE II

| Amount of Solution Added (ml/kg soil) | Reniform Nematodes per 100 cc of Soil | | | | |
|---|---|---|---|---|---|
| Composition | 0.0 | 0.1 | 0.2 | 0.4 | 0.8 |
| D | 212 | 153 | 5 | 0 | 0 |
| E | 212 | 278 | 34 | 0 | 0 |
| F | 212 | 190 | 227 | 118 | 11 |

This example shows that for reniform nematode control the combination of furfural and methyl isothiocyanate provides decidedly more effectiveness than either furfural or methyl isothiocyanate alone, when applied at low dosage rates, e.g., about 0.1 ml/kg of soil. For example, at the 0.1 ml/kg soil level, the use of Composition D resulted in about a 27% reduction in the number of reniform nematodes, the use of Composition E resulted in about a 31% increase in the number of reniform nematodes and the use of Composition F resulted in about a 10.3% reduction in the number of reniform nematodes.

EXAMPLE 3

This example compares the nematicidal activity of nematicidal compositions containing furfural-metham sodium mixture (Composition G), furfural (Composition H) and metham sodium, a precursor of methyl isothiocyanate (Composition I) as the active ingredient(s). The source of the metham sodium was a commercial product containing 42% metham sodium, sold by Zeneca, Inc. under the trademark Vapam®. The test compositions used in this example were emulsions prepared with polyoxyethylene sorbitan monolaurate emulsifier sold by Aldridge Company under the trademark Tween® 20. The treatment emulsions used in this example were prepared as follows. Composition G is an aqueous emulsion containing 5% furfural and 0.42% metham sodium, prepared by mixing 1 ml of Tween® 20, 10 mls of furfural and 2 mls of Vampam® and diluting the mixture to a final volume of 200 mls with demineralized water; Composition H is an aqueous emulsion containing 5% furfural, prepared by thoroughly mixing 1 ml of Tween® 20 with 10 mls of furfural and diluting the mixture to a final volume of 200 mls with demineralized water; and Composition I is an aqueous emulsion containing 0.42% metham sodium, prepared by mixing 1 ml of Tween® 20 with 2 mls of Vampam® and diluting the mixture to a final volume of 200 mls with demineralized water.

The soil used in this example was a cotton field soil infested with lance (Hoplolamus galeatus) nematodes and microbivorous (beneficial) nematodes. One kg soil samples were prepared according to the procedure described in Example I.

The experiments were carried out by applying the emulsions to soil samples at dosage rates of 0, 1, 2, 3 and 4 mls per kg of soil. These dosage rates correspond, respectively, to 0.0, 0.0542, 0.1084, 0.1626, and 0.2168 ml of furfural-metham sodium mixture (Composition G) per kg of soil; 0.0, 0.05, 0.10, 0.15, and 0.20 ml of furfural (Composition H) per kg of soil; and 0.0, 0.0042, 0.0084, 0.0126, and 0.0168 ml of metham sodium (Composition I) per kg of soil. Thus, at each concentration level the concentration of a given component in Composition G was equal to the concentration of that component in Composition H or Composition I. There were 7 replications of each dosage. The soil samples were maintained in the moistened state for 2 weeks, after which 100 cc quantities of each sample were taken and analyzed according to the procedure described in Example I. The average number of live nematodes in the replicated experiment for each treatment concentration was determined and recorded in Table III.

TABLE III

| Amt. Of Solution Added (ml/kg soil) Composition | 0.0 | 1.0 | 2.0 | 3.0 | 4.0 |
|---|---|---|---|---|---|
| | Lance Nematodes per 100 cc of Soil | | | | |
| G | 11 | 6 | 0 | 0 | 0 |
| H | 11 | 30 | 12 | 4 | 1 |
| I | 11 | 17 | 5 | 0 | 0 |
| | Microbivorous Nematodes per 100 cc of Soil | | | | |
| G | 415 | 248 | 262 | 59 | 6 |
| H | 415 | 293 | 353 | 449 | 359 |
| I | 415 | 279 | 202 | 141 | 81 |

This example shows that for lance nematode control the combination of furfural and metham sodium provides decidedly more effectiveness than either furfural or metham sodium alone, when applied at low dosage rates, e.g., about 1.0 ml/kg of soil. For example, at the 1.0 ml/kg soil level, the use of Composition G resulted in about a 45% reduction in the number of lance nematodes, the use of Composition H resulted in about a 173% increase in the number of lance nematodes and the use of Composition I resulted in about a 54.5% increase in the number of lance nematodes. The data in Table III also indicates that at lower dosage rates (1.0 and 2.0 mls/kg of soil), fewer than half of the beneficial microbivorous nematodes originally in the soil were destroyed. Furthermore, the data also indicates that at the 1.0 ml/kg of soil dosage rate, only 167 microbivorous nematodes were destroyed using Composition G, whereas a total of 258 microbivorous nematodes were destroyed by the use of Compositions H and I separately (122 by Composition H and 136 by Composition I); and at the 2.0 mls/kg of soil dosage rate, only 153 microbivorous nematodes were destroyed using Composition G, whereas a total of 275 microbivorous nematodes were destroyed by the use of Compositions H and I separately (62 by Composition H and 213 by Composition I).

Although the invention has been described with particular reference to specific compositions and to specific experiments, these features are merely exemplary of the invention and variations are contemplated. The scope of the invention is limited only by the breadth of the appended claims.

INDUSTRIAL APPLICABILITY

The invention has applicability in the field of agriculture. Specifically, the invention is used to control or eliminate insects and nematodes that are parasitic to farm crops, ornamental plants and various other vegetative materials. The method of the invention is practiced by applying the compositions of the invention to plant pests, preferably pests that infest growth media, such as soil. The compositions are preferably applied to the growth media not later than about ten days prior to planting crops, seeds or plants in the growth material.

What is claimed is:

1. A composition consisting essentially of (a) at least one formyl cyclic ether containing up to 12 carbon atoms, selected from formyl furans, formyl pyrans or mixtures thereof, and (b) at least one isothiocyanate or precursor thereof containing 2 to 14 carbon atoms.

2. The composition of claim 1, wherein component (a) is furfural, 2,5,-diformyl furan, at least one formyl pyran, formyl tetrahydrofuran, or mixtures thereof, and component (b) is methyl isothiocyanate, ethyl isothiocyanate, propyl isothiocyanate, butyl isothiocyanate, allyl isothiocyanate, mustard oil, phenyl isothiocyanate, benzyl isothiocyanate, sodium N-methyldithiocarbamate, tetrahydro-3,5-dimethyl-2H-1,3,5-thiadiazin-2-thione or mixtures thereof.

3. The composition of claim 1, wherein component (a) is furfural, 2,5-diformyl furan, formyl tetrahydrofuran, or mixtures thereof.

4. The composition of claim 3, wherein component (b) is methyl isothiocyanate, allyl isothiocyanate, mustard oil, phenyl isothiocyanate, sodium N-methyidithiocarbamate, tetrahydro-3,5dimethyl-2H-1,3,5-thiadiazin-2-thione, or mixtures thereof.

5. The composition of claim 4, wherein component (a) is furfural.

6. The composition of claim 3, wherein component (b) is methyl isothiocyanate, allyl isothiocyanate, mustard oil or mixtures thereof.

7. The composition of any one of claims 1, 4 or 5, wherein about 50 to about 99.5 parts of component (a) and about 0.5 to about 50 parts of component (b) per each 100 total parts of component (a) and component (b) are present in said composition.

8. A method of controlling plant pests comprising introducing the composition of any one of claims 1, 4 or 5 into an environment containing said plant pests.

9. The method of claim 8, wherein said composition is introduced into said environment with a carrier system for component (a), for component (b) or for both component (a) and component (b).

10. The method of claim 9, wherein said composition is intruduced into said environment in the form of a solution, a suspension or an emulsion.

11. The method of claim 10, wherein said composition is introduced into said environment with a carrier system comprising water, an organic compound or combinations thereof.

12. The method of claim 8, carried out by applying said composition to plant growth medium containing said plant pests.

13. The method of claim 12, wherein said composition is applied to said plant growth medium prior to planting plants or plant seeds therein.

14. The method of claim 12, comprising separately applying component (a) and component (b) to said plant growth medium.

15. The method of claim 12, wherein said plant pests comprise nematodes.

16. The method of claim 12, wherein component (a) is furfural and component (b) is methyl isothiocyanate, allyl isothiocyanate, mustard oil or mixtures thereof.

17. The method of claim 12, wherein about 50 to about 99.5 parts of component (a) and about 0.5 to about 50 parts of component (b) per each 100 total parts of component (a) and component (b) are present in said composition.

18. The method of claim 17, wherein said plant growth medium comprises soil.

19. The method of claim 18, wherein a sufficient amount of said composition is applied to said plant growth medium to provide a concentration of about 0.1 to about 1000 parts by weight of component (a) and component (b) per each million parts by weight of medium being treated.

20. The method of claim 19, wherein said sufficient amount of said composition is applied to said medium to provide a concentration of about 0.5 to about 500 parts by weight of total component (a) and component (b) per each million parts by weight of medium being treated.

21. The method of claim 17, wherein component (a) is furfural and component (b) is methyl isothiocyanate, allyl isothiocyanate, mustard oil, or mixtures thereof, and sufficient composition is applied to said soil to provide a dosage of about 2 to about 500 kg of (a) plus (b) per each hectare of soil being treated.

22. The composition of claim 1, wherein component (a) is at least one formyl furan.

23. The composition of any one of claims 1, 2 or 4, wherein component (a) contains up to 8 carbon atoms.

24. The composition of claim 5, wherein component (b) is methyl isothiocyanate, allyl isothiocyanate, mustard oil or mixtures thereof.

25. The composition of claim 5 or 24, wherein about 80 to about 97 parts of component (a) and about 3 to about 20 parts of component (b) per each 100 total parts of component (a) and component (b) are present in said composition.

26. A composition consisting essentially of (a) at least one formyl cyclic ether containing up to 12 carbon atoms, selected from formyl furans, formyl pyrans or mixtures thereof; (b) at least one isothiocyanate or precursor thereof containing 2 to 14 carbon atoms; and (c) a carrier system for component (a), for component (b) or for both component (a) and component (b).

27. The composition of claim 26, in the form of a solution, a suspension or an emulsion.

28. The composition of claim 27, wherein said carrier system is water, an organic solvent, emulsifying agent, or combinations thereof.

29. A composition of claim 26 wherein component (b) is methyl isothiocyanate, allyl isothiocyanate, mustard oil, phenyl isothiocyanate, sodium N-methyldithiocarbamate, tetrahydro-3,5-dimethyl-2H-1,3,5-thiadiazin-2-thione or mixtures thereof.

30. A composition of claim 29 wherein component (a) is furfural.

* * * * *

UNITED STATES PATENT AND TRADEMARK OFFICE
CERTIFICATE OF CORRECTION

PATENT NO. : 6,720,352 B1
DATED : April 13, 2004
INVENTOR(S) : Rodrigo Rodriguez-Kabana It is certified that error appears in the above-identified patent and that said Letters Patent is hereby corrected as shown below:

Title page,
Insert Item:

-- [73] Assignee: Illovo Sugar Limited, Mount Edgecombe, South Africa --.

Column 6,
Line 13, change "bis(issthiocyanate)" to -- bis(isothiocyanate) --;
Line 18, change "N-methyidithiocarbamate" to -- N-methyldithiocarbamate --;
Lines 33-34, change "1,3-clohexane" to -- 1,3-cyclohexane --.

Column 12,
Line 55, change "N-methyidithiocarbamate" to -- N-methyldithiocarbamate --.

Column 13,
Line 13, change "comprising water, an organic compound" to -- which is water, an organic --.
Line 40, change "claim 19, wherein said" to -- claim 18, wherein a --.
Line 41, before "medium" insert -- plant growth --.

Column 14,
Line 17, before "24" insert -- claim --.
Line 28, change "claim 26" to -- any one of claims 26, 29, or 30 --.
Line 31, cancel "emulsifying agent".

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,720,352 B1
DATED : April 13, 2004
INVENTOR(S) : Rodrigo Rodriguez-Kabana It is certified that error appears in the above-identified patent and that said Letters Patent is hereby corrected as shown below:

<u>Column 13,</u>
Line 13, change "comprising water, an organic compound" to -- which is water, an organic solvent --.

Signed and Sealed this

Fifth Day of April, 2005

JON W. DUDAS
*Director of the United States Patent and Trademark Office*